(12) United States Patent
Greenburg et al.

(10) Patent No.: US 8,583,455 B2
(45) Date of Patent: Nov. 12, 2013

(54) PATIENT DIABETES DATA INTERCHANGE WITH ELECTRONIC MEDICAL RECORDS

(75) Inventors: Alan M. Greenburg, Indianapolis, IN (US); Brittany A. Dressler, Indianapolis, IN (US); Igor Gejdos, Indianapolis, IN (US); Anthony J. Butt, Noblesville, IN (US); Kristin Davenport, Fortville, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 575 days.

(21) Appl. No.: 12/233,882

(22) Filed: Sep. 19, 2008

(65) Prior Publication Data

US 2010/0076784 A1   Mar. 25, 2010

(51) Int. Cl.
 *G06Q 10/00* (2012.01)
(52) U.S. Cl.
 USPC .................................................. 705/3; 705/2
(58) Field of Classification Search
 USPC ........................................................... 705/2
 See application file for complete search history.

(56) References Cited

U.S. PATENT DOCUMENTS

| | | | |
|---|---|---|---|
| 5,890,129 A | 3/1999 | Spurgeon | |
| 6,408,303 B1 | 6/2002 | Richards | |
| 7,072,725 B2 | 7/2006 | Bristol et al. | |
| 7,089,247 B2 | 8/2006 | Kloos et al. | |
| 7,092,891 B2 * | 8/2006 | Maus et al. | 705/2 |
| 2002/0083075 A1 | 6/2002 | Brummel et al. | |
| 2003/0069758 A1 | 4/2003 | Anderson et al. | |
| 2004/0088317 A1 * | 5/2004 | Fabrick et al. | 707/102 |
| 2006/0101063 A1 | 5/2006 | Schreeder et al. | |
| 2006/0136197 A1 * | 6/2006 | Oon | 704/9 |
| 2007/0088564 A1 | 4/2007 | March, Jr. et al. | |
| 2008/0071580 A1 * | 3/2008 | Marcus et al. | 705/3 |
| 2008/0097910 A1 * | 4/2008 | Dicks et al. | 705/50 |
| 2008/0249805 A1 * | 10/2008 | Singh | 705/3 |

FOREIGN PATENT DOCUMENTS

WO   2005000004 A2   1/2005

OTHER PUBLICATIONS

Accu-Chek Spirit Insulin Pump System Pocket Compass Software with Bolus Calculator User Guide.
Weinstock, Ruth S., et al., "Pharmacy Costs and Glycemic Control in the Department of Veterans Affair", Diabetes Care, vol. 27, Supplement 2, May 2004, pp. B74-B81.

* cited by examiner

*Primary Examiner* — Hiep V Nguyen
(74) *Attorney, Agent, or Firm* — Dinsmore & Shohl LLP

(57) ABSTRACT

A system and method for transferring patient diabetes information into an electronic medical record on a health record system with user validation are disclosed. After testing a patient's blood glucose levels over a period of time with a blood glucose meter which stores the patient diabetes information and the blood glucose levels in a first electronic format record, and after a user transfers the first electronic format record from the blood glucose meter into a diabetes management system on a computer, the invention provides a service which automatically monitors an output folder to determine when an export file containing the patient diabetes information is stored therein and after detection, automatically processes the export file into a default electronic medical report which can be copied into a clipboard utility provided by the computer and pasted into the electronic medical record of the patient on the health record system.

14 Claims, 8 Drawing Sheets

PATIENT DIABETES DATA INTERCHANGE WITH ELECTRONIC MEDICAL RECORDS

FIELD OF THE INVENTION

The present invention relates generally to electronic medical records and in particular to a method and system for automating the transferring of patient diabetes information into electronic medical records on a health record system with user validation.

BACKGROUND OF THE INVENTION

Currently home testing glucose data is either not entered into a permanent electronic medical record on a health record system, such as for example, of a clinic, health care provider, hospital, and the likes, or it is manually typed in as observed from either a device providing the glucose data or an application running on a user's computer to which the glucose data has been provided by the device. By not having this data in a health record system, if not entered, clinicians are not able to view the glucose data of the patient since the last visit to them. This data is important in the overall care and treatment plan of diabetic patients. If data is manually entered into the health record system, there is the risk of transcription errors and also timing factors. Depending on the number of patients seen, manually typing the data into such a health record system may take up to several hours per day.

One prior art solution is to use a $3^{rd}$ party application which exports patient glucose data from a home testing device into a spreadsheet application, such as MS Excel, that is then cut and pasted into a notes field provided in the electronic medical record of the person in a health record system. However, the prior art solution is not compatible with all home testing devices providing patient glucose data and which have no usable export file for data manipulation and/or an interface allowing such data to be transferred from such devices into a health record system. With such incompatible device, users must manually type the information shown on the device into the notes field of the selected electronic medical record if such data is to be available in the health record system.

Additionally, with the prior art solution, a spreadsheet application must be provided on the users computer along with the understanding of using such an application, potentially by persons not typically familiar such programs. Furthermore, if the clipboard in spreadsheet application is not cleared at the end of each file handling, there is a chance that the user may be looking at one patient's data, but paste the previous patient's data into the current patient's electronic medical record. If such an error is not caught, in addition to corrupting the data in the electronic medical record, the risk to patient is greatly increased.

SUMMARY OF THE INVENTION

It is against the above background that the present invention provides a method and system for electronically transferring of patient diabetes information into electronic medical records on a health record system with user validation.

In one embodiment, a method for formatting and transferring patient diabetes data into an electronic medical record on a health record system with user validation is disclosed. After testing a patient's blood glucose levels over a period of time with a blood glucose meter which stores the patient diabetes data containing blood glucose levels in a first electronic format and after a user transfers the patient diabetes data from the blood glucose meter into a patient record provided by a diabetes management system on a compute, creates an export file which provides the patient diabetes data in a second electronic format and stores the export filed to an output folder, the method comprises these following steps: providing an interface service which automatically monitors the output folder to determine when the export file is provided thereto; and automatically detecting with the service the export file when provided to the output folder. After detection, the method further comprises automatically parsing and formatting with the interface service the export file into formatted patient diabetes data according to a pre-defined report template; automatically opening a dialog box which displays the formatted patient diabetes data; copying the displayed formatted patient diabetes data into a clipboard utility provided by the computer; selecting and displaying the electronic medical record of the patient in a client application of the health record system provided on the computer; and pasting and displaying the formatted patient diabetes data in the electronic medical record of the patient.

In another embodiment, a computer system which implements the above described method as well as in still another embodiment a computer readable medium providing instructions which will configured a computer system to implement the above described method are also disclosed.

These and other advantages and features of the invention disclosed herein, will be made more apparent from the description, drawings and claims that follow.

BRIEF DESCRIPTION OF THE DRAWINGS

The following detailed description of the embodiments of the present invention can be best understood when read in conjunction with the following drawings, where like structure is indicated with like reference numerals, and in which:

FIG. 5 is a screen shot image of a File Display dialog box according to an embodiment of the present invention and depicts the main graphical user interface to interact with the interface utility of FIG. 3;

DETAILED DESCRIPTION

Diabetes is a metabolic syndrome wherein the physiology of the body is not functioning normally to regulate blood glucose for various etiological reasons. For diabetes care, glucose measurements normally obtained using a glucose meter are the primary parameters for conducting therapy management. There are several secondary parameters relevant for managing diabetes, such as HbA1C, ketones, and FFA. However, such measurements are not needed on a regular basis. In addition, there is information about activities (such as the amount and execution rates for meal consumption and exercise) that is important in adjusting and correcting therapy.

To manage the disease, there are many diabetes management inputs, utility tools, and devices used to capture patient activity and assist in insulin therapy which need to interact and exchange information for determining and evaluating effectiveness of prescribed insulin therapy. For example, typical disease management components include: personal computers, centralized databases for data management, algorithms providing procedures for managing pump infusion based on user inputs, glucose measurements, and insulin-delivered amounts, user inputs via user interface, measurements, tests, etc., healthcare professional (HCP) inputs (e.g., inputs from physicians, nurses, medical technologists, and medical office personnel, etc.) via user interface, measurements, tests, and insulin pumps, blood glucose (bG) meters, and other handheld devices which may be either integrated or standalone devices that function independently.

The present invention helps to improve the interaction of health record systems with devices that collect patient diabetes data in incompatible file formats. In general, a system and method for transferring patient diabetes information into an electronic medical record on a health record system unable to directly accept data from devices collecting the patent diabetes information in a native format are discussed hereafter.

Figure 1:
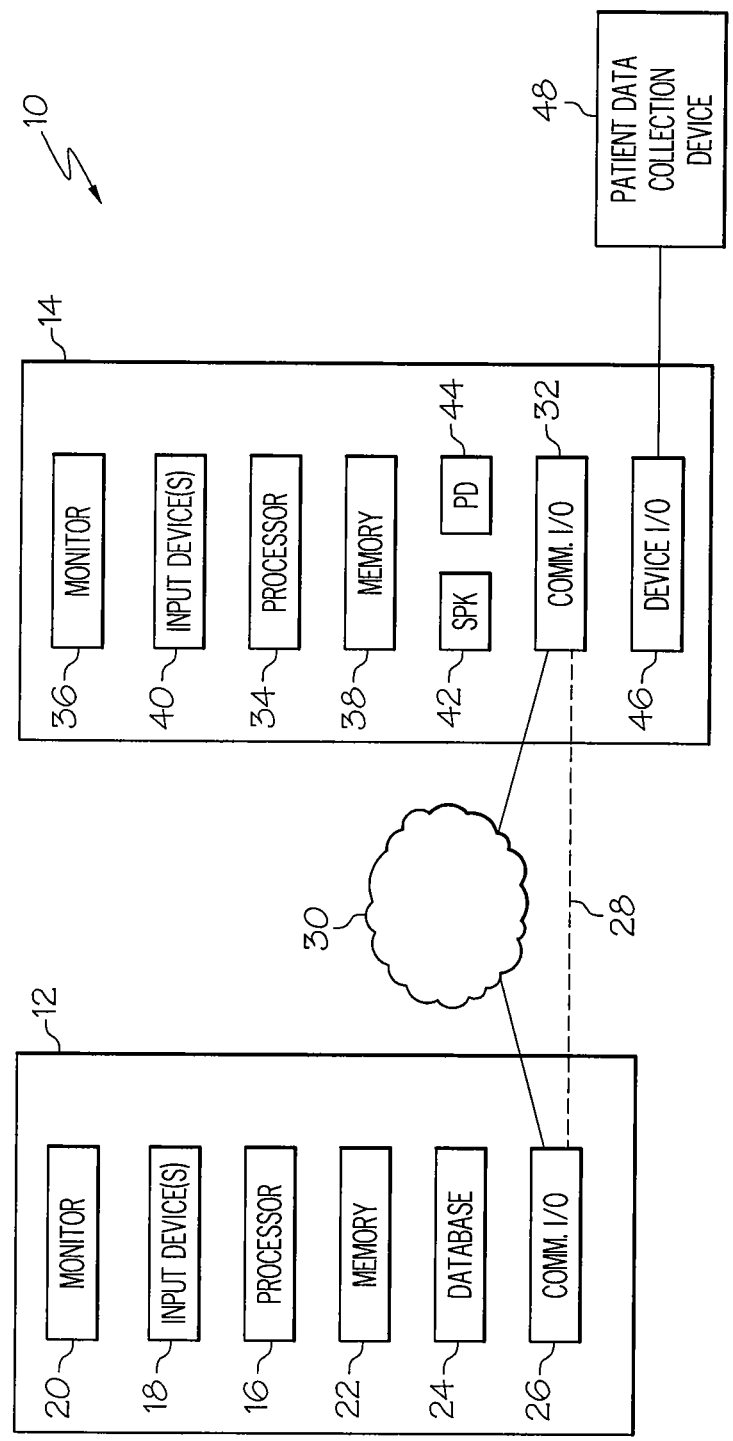
FIG. 1 is a block diagram of a hardware-software system that operates in a typical client-server environment which may be used to employ the present invention in helping to facilitate improved diabetes care management of patients.

As is illustrated in block diagram by FIG. 1, a hardware-software system that operates in a typical client-server environment running on a PC platform may be used to employ the present invention. In one embodiment, components of the overall system may be distributed geographically and accessible via an intranet and/or Internet. In the illustrated embodiment, the system 10 provides a server computer 12 and a client computer 14. The server computer 12, in one embodiment is the health record system, which includes a conventional processor 16 that is operatively connected to an input device 18, a monitor 20, and memory 22 (e.g., RAM, ROM, and hard drive(s)). The input device 18 may be any one or a combination of a conventional keyboard, a conventional point-and-click device, microphone, or the like, and the monitor 20 may be any conventional computer monitor. The processor 16 of the server computer 12 is also operatively connected to a database 24 that may be internal to the server computer 12, or may alternatively be external to the server computer 12. The processor 16 of the server computer 12 is further operatively connected to a conventional communication interface 26. Devices, such as a bus (not shown), interconnect the above mentioned components as is known in the art.

The client computer 14 likewise includes a conventional processor 34 that is operatively connected to a conventional monitor 36, conventional memory 38 (e.g., RAM, ROM, and hard drive(s)), and a conventional input device 40 which may be any one or a combination of a conventional keyboard, a conventional point-and-click device, microphone, or the like. Alternative, input may also be via the monitor 36 in embodiments wherein the monitor 36 includes one or more touch-screen buttons or switches. The client computer 14 may further include one or more conventional speakers 42 operatively connected to the processor 34. The processor 34 of the client computer 14 is further operatively connected to a device interface 46 that is configured to be operatively connected, either wirelessly or via a wired connection, to one or more external devices.

In one embodiment, for example, the device interface 46 may be or include a conventional input/output port configured for wired connection to an external device. Examples of such a conventional input/output port include, but should not be limited to, a conventional universal serial bus (USB) port, a conventional RS-232 port, or the like. Alternatively or additionally, the device interface 46 may be or include a conventional wireless transceiver configured to wirelessly communicate with a similar transceiver of an external device. Examples of such a wireless transceiver include, but should not be limited to, an infra-red (IR) transceiver, a radio frequency (RF) transceiver, an inductive transceiver, an acoustic transceiver or the like.

The processor 34 of the client computer 14 provides information to, or receives information from, an external patient data collection device 48, such as in the form of a patient data measurement and/or collection device, via the device interface 46. Examples of the patient data measurement and/or collection device 48 may include, but should not be limited to, a blood or tissue glucose sensor or other glucose measurement device, a body temperature sensing or measurement device, a body weight measuring device, a blood pressure monitoring device, an HbA1C monitoring device, an implantable or externally worn drug infusion pump, e.g., for administration of insulin or one or more other blood glucose lowering or raising drugs, a handheld or other data collection device for monitoring patient meal intake data, patient exercise data, patient illness data, etc., or the like.

The processor 34 of the client computer 14 is further operatively connected to a conventional communication interface 32. The communication interfaces 26 and 32 may be any conventional communication interfaces that provide for electronic communications between the server computer 12 and the client computer 14. In the illustrated embodiment, for example, the communication interfaces 26 and 32 are configured to provide for electronic communications between the server computer 12 and the client computer 14 via the World Wide Web (WWW), internet and/or intranet in a conventional manner. Alternatively or additionally, the communication interfaces 26 and 32 may be or include telephone modems so that the server computer 12 and the client computer 14 may communicate via telephone. This disclosure contemplates that electronic communications between the server computer 12 and the client computer 14 may alternatively be accomplished via other conventional wired or wireless communications links. In any case, it will be understood that the system 10 may include multiple networked server computers 12 that may or may not be distributed geographically, and that each server computer 12 may serve multiple client computers 14 that may be distributed geographically. In addition, the processes (i.e., software portion) of the present may be configured on the client side or the server side, depending on the particular use case scenario.

Figure 2:
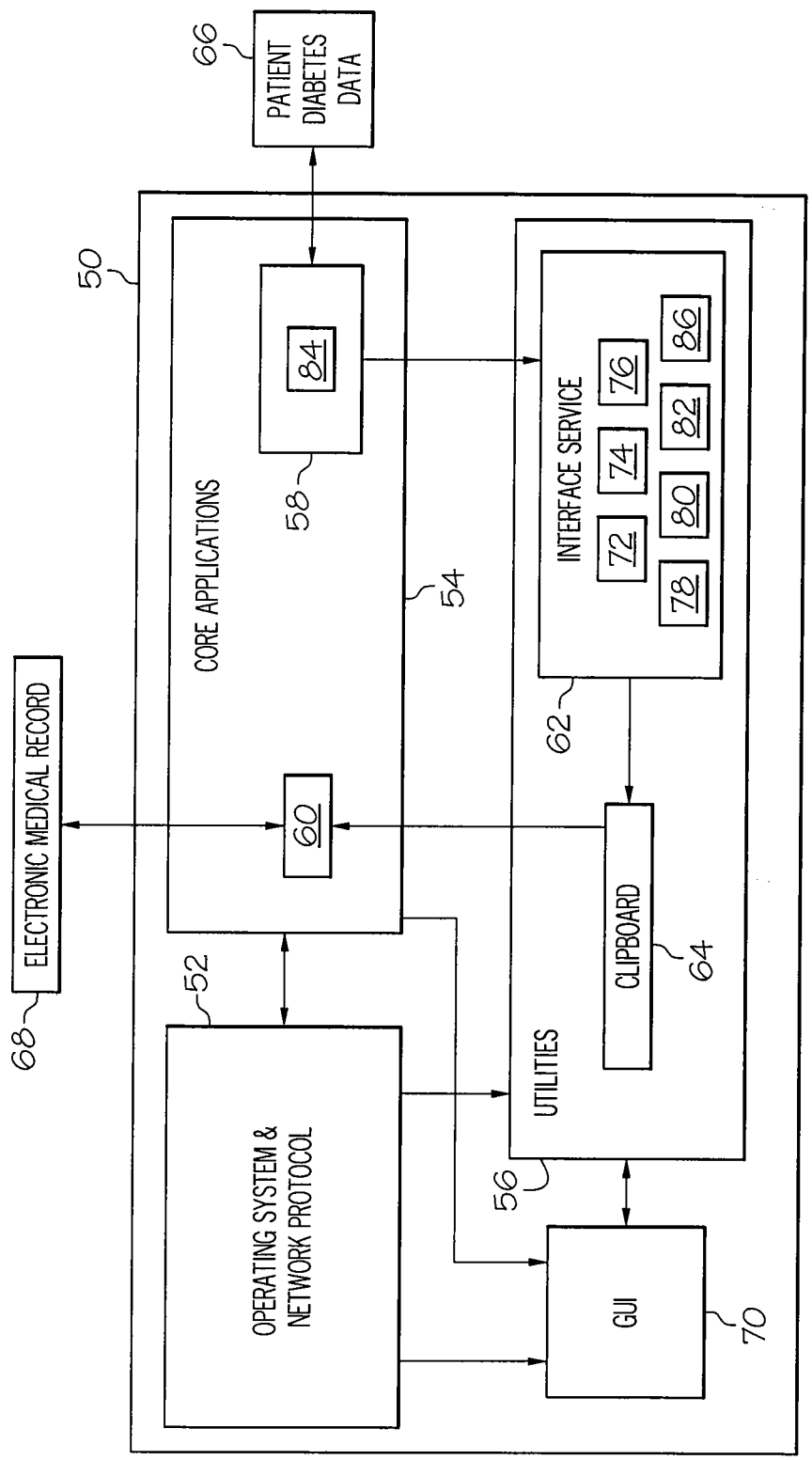
FIG. 2 is a block diagram of a software embodiment used in the system of FIG. 1 according to the present invention.

With reference to FIG. 2, one illustrative embodiment of software 50 used by the system 10 of FIG. 1 is shown. The software 50 will be understood to be configured in a conventional manner to allow for appropriate interaction between the client computer 14 and the server computer 12 for performing user authentication, acquiring and/or storing data in a database and conducting ancillary activities such as background processing of data, automation of triggering events, and the like. In the illustrated embodiment, the software 50 includes a conventional operating system 52 (with an included network protocol portion), core applications 54, and utilities 56.

The operating system 52 as well as the network protocol portion is configured in a conventional manner to allow interaction between the various computers, devices and/or databases. In one embodiment, the operating system is the Microsoft Windows operating system, and in other embodiments may be any other suitable operating system, such as Mac OS, Linux, and Solaris, which all provide a conventional clipboard utility. The core applications and utilities 54 and 56, respectively, may reside on the server computer 12, the client computer 14, or at least in part on both.

Generally, the core applications 54 comprises a conventional diabetes management software 58 and a client application 60. As one specific example, the diabetes management software 58 in one embodiment is the Accu-Chek CAMIT Pro software provided by Roche Diagnostics, which provides a data interface to various patient data collection devices as well as data management, analysis, and reporting features which helps healthcare professionals manage and provide effective patient diabetes care. The client application 60 is any conventional application for opening and viewing electronic medical records stored in a database of a health record system. In one embodiment, the database is database 24 of server computer 12 (FIG. 1). In one embodiment, server computer 12 is the Veterans Health Administration's CPRS/VistA health record system, which provides an electronic health record (EHR) module refers to as the Computerized Patient Record System (CPRS). It is to be appreciated that VistA is the database system that stores the Veterans Health Administration's patient information, and CPRS is the windows client that provides user with access to all functional modules in the VistA database system which is able to consolidate patient information from different modules. Accordingly, for this example and in one embodiment, the client application 60 is the CPRS client application, provided by the Veterans Health Administration, which connects to the VistA health record system (e.g. sever computer 12) via the Internet 30 to provide access to the electronic medical records in database 24 of patients.

The utilities 56 include at least an interface service 62 and clipboard 64. As known, the clipboard 64 is a conventional software program that is used for short-term storage of data as it is transferred between documents or applications (e.g., diabetes management software 58 and client application 60), via copy and paste operations. The clipboard 64 is usually implemented as an anonymous, temporary block of memory (e.g., memory 38) that can be accessed from most or all programs within a graphical user interface (GUI) environment 70 provided by the operating system 52 as is known. As will be discussed in greater details later hereafter, the core applications 54 and utilities 56 are interacted by the user also in the GUI environment 70.

In one embodiment, the software 50 is intended to be used on computers that are used in hospitals and clinics by healthcare professionals including diabetes nurse educators and endocrinologists. As such, the interface service 62 in one embodiment facilitates an electronic transfer of patient diabetes data 66, collected by the patient data collection device 48 (FIG. 1) and downloaded to the diabetes management software 58 during scheduled hospital and clinic visits, to an electronic medical record 68 provided in a database e.g., generally, database 24, or specifically, in one embodiment, the VistA health record system. The electronic medical record 68 is accessed, opened, and edited via the client application 60 which is running on the same computer (i.e., client computer 14) as the diabetes management software 58. Accordingly, since both applications may be interacted with in the same GUI environment 70, the patient diabetes data provided to the clipboard 64, via the interface service 62, can be pasted into the electronic medical record 68 that is opened by the client application 60. In one embodiment, the patient diabetes data 66 is pasted as text from the clipboard 64 into a text field of the electronic medical record 68 such as, for example, in one embodiment, the Progress Notes field provided in the EHR of the CPRS/VistA health record system (e.g., server computer 12).

Examples of the types of information which may be provided as the patient diabetes data 66 include, but are not limited to, patient self-testing blood or tissue glucose measurements as a function of time, of patient body temperature measurements as a function of time, of ambient temperature measurements (around the body of a patient) as a function of time, of patient heart rate and/or pulse rate as a function of time, of patient blood pressure as a function of time, of one or more other patient physiological condition parameters such as weight, menses, stress, illness, and the like, of meal or snack, i.e., carbohydrate intake, information as a function of time, of patient physical activity as a function of time, of insulin delivery information over time, of intervention information as a function of time, specific information about one or more of meal intake, exercise performance, and the like, use of specialized instruments and/or devices, and the like. Such patient diabetes data 66 provided to the electronic medical record 68 of a patient in the above described manner helps to provide a more complete electronic medical record and documentation of the patient's glucose compliance, saves time from the current manual data entry process that can take up to the time of one fully time employee to manually enter data from all patients seen in a clinic, and minimizes the risk of errors in the charting, resulting from manual transcription of the data from a separate application into the electronic medical record. Furthermore, the interface service 62 does not change or modify the existing diabetes management software 58 or the client application 60.

It is to be appreciated that FIG. 2 also depicts the context in which the software 50 is deployed and used. It shows the relationships of the software to external applications and processes, and tells how the core application 54 and utilities 56 interact in the GUI environment 70. As also depicted, the interface service 62 provides a user interface module 72, a file discovery module 74, a patient data formatting module 76, configuration module 78, an error logging module 80, and an installation module 82.

The user interface module 72 implements the user interface on the client computer 14. This module 72 allows users to view parsed patient data, allows users to change the current template and number of days, and allows users to send parsed patient data to the clipboard 64 as will be explained in later sections.

The file discovery module 74 implements a discover function on the client computer 14 for export files containing the patient diabetes data 66 downloaded to the diabetes management software 58 from patient data collection device 48. This module 74 monitors an export directory of the diabetes management software 58 for new export files, such as provided with a particle file extension. In one embodiment, the file extension is .RDM, which is the file extension used by the export files of the Accu-Chek CAMIT Pro software. The filed discovery module 74 also monitors the currently configured export directory settings in the diabetes management software 58, and maintains a list of files to parse when there are new exports while the interface service 62 is busy with another file.

The patient data formatting module 76 contains the implementation of the patient data parsing and formatting functions of the interface service 62, and is responsible for parsing the patient diabetes data in the current export file 84 containing the patient diabetes data 66, and formatting the parsed patient data according to a template 86. The template 86 provides the layout for displaying the parsed patient data in the GUI environment 70.

The configuration module 78 contains the classes and interfaces used by the interface service 62 to read, set, and manage service configuration settings/defaults. The error logging module 80 contains the classes and interfaces used by the interface service 62 to log application/service errors. The installation module 82 implements the requirements for successful deployment and initial configuration of the interface service (as a software application) by validating the target PC meets the minimum requirements, and allows the user to set the configuration settings/defaults.

It is to be appreciated that in one embodiment, the interface service 62 runs as a windows system tray applications and monitors for new export files from the diabetes management application 58. When new exports files are found, the interface service 62 parses the patient data contained in the export file 84 and displays the data in a File Display dialog box 111 (FIG. 5) according to a default report template 112 and a default date range 133 as configured and explained in great details in a later section.

Figure 3:
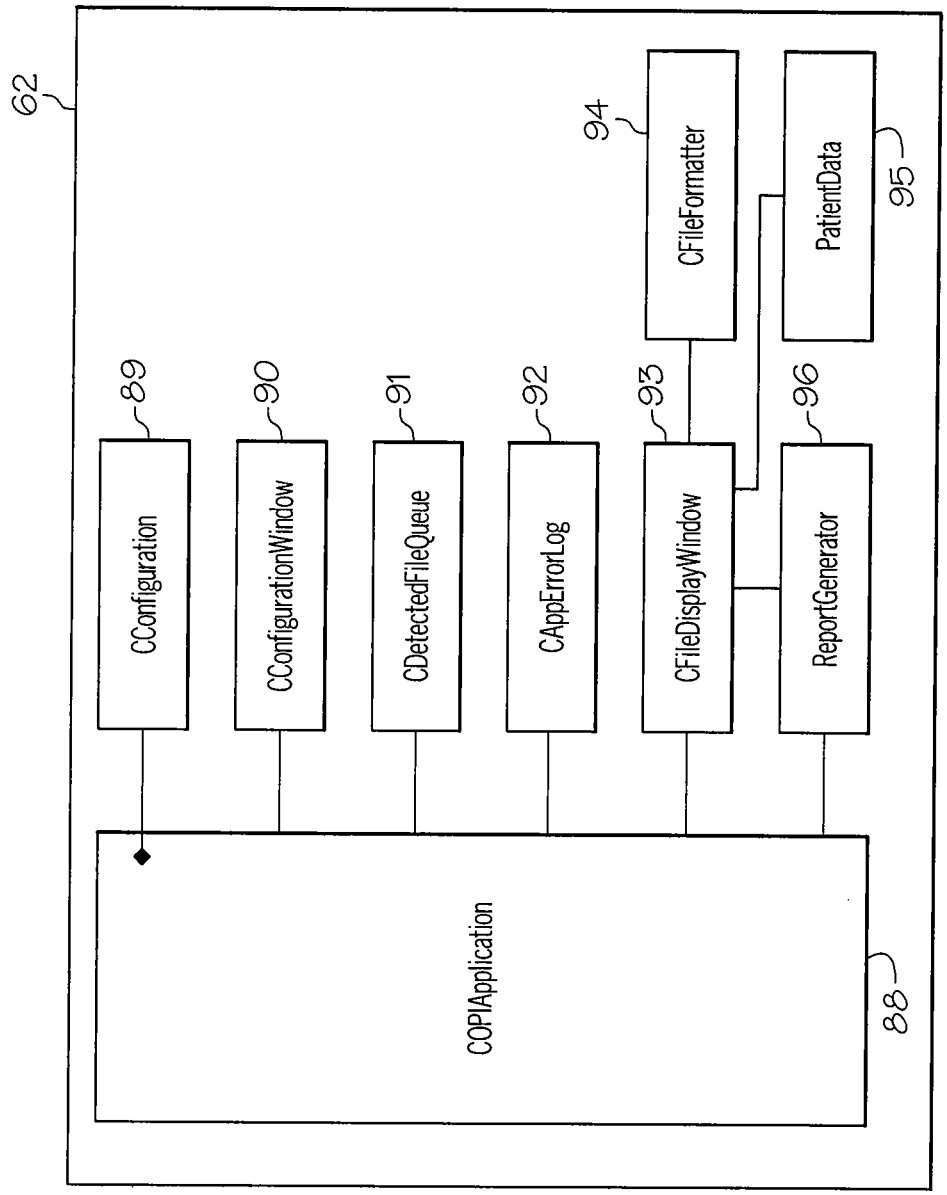
FIG. 3 is a class diagram of interface utility embodiment used in the software embodiment of FIG. 2 according to the present invention.
Figure 5:
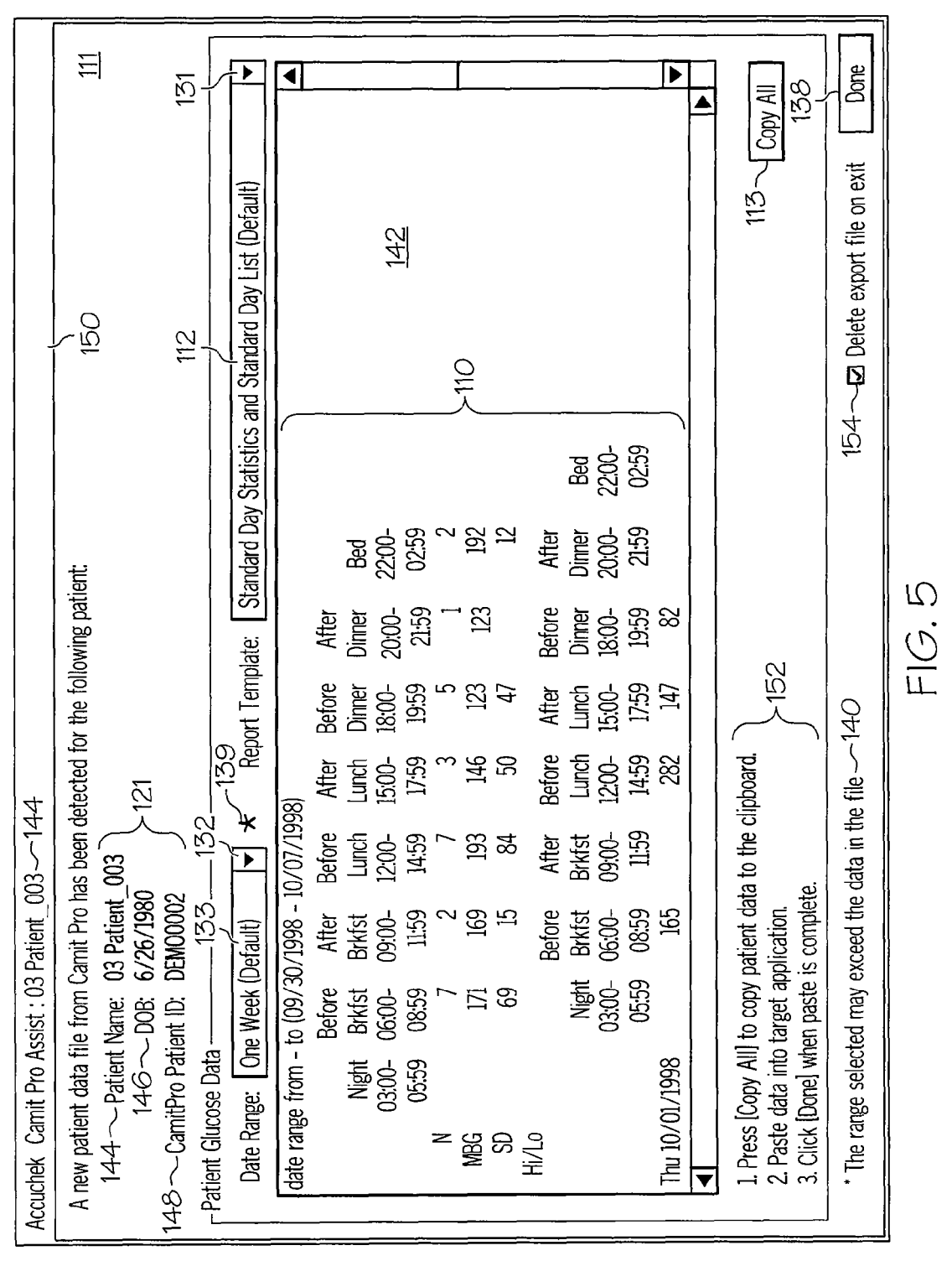
Figure 6:
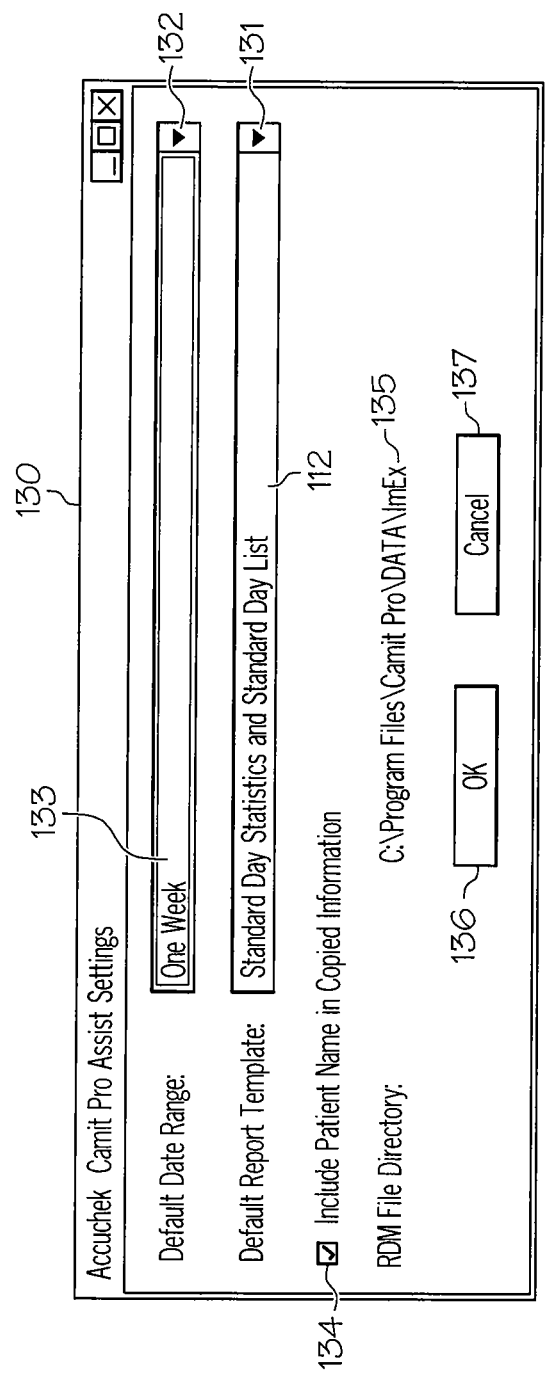
FIG. 6 is a screen shot image of a Configuration Options dialog box according to an embodiment of the present invention and depicts the graphical user interface to configure the interface utility of FIG. 3.

With reference to FIGS. 3, 5 and 6, a class diagram detailing the object classes to provide the above mentioned modules of the interface service 62 is shown. In particular, the classes provided are: COPIApplication class 88, CConfiguration class 89, CConfigurationWindow class 90, CDetectedFileQueue class 91, CAppError Log class 92, CFileDisplayWindow class 93, CFileFormatter class 94, PatientData class 95, and ReportGenrator class 96.

The COPIApplication class 88 provides the entry points for the interface service 62 and puts the application in the system tray of the operating system 52. The COPIApplication class 88 also provides access to a Configuration Options dialog box 130 (FIG. 6). The COPIApplication( ) object call initializes the interface service 62 and all the classes properties, where: Configuration is the instance of the CConfiguration class 89 used to store the current configuration options; ConfigurationWindow is the instance of the CConfigurationWindow class 90 used to hold a reference to the Configuration Options dialog box 130; DetectedFileQueue is the instance of the CDetectedFileQueue class 91 used by the interface service 62 to collect references to new export files of a particular extension (e.g., .RDM) found in the Export File Directory location 135 while a current file is still being processed; and FileDisplayWindow is the instance of the CFileDisplayWindow class 93 used to hold a reference to the File Display dialog box 111.

The CConfigurationWindow class 90 as mentioned above holds a reference to and provides the Configuration Options dialog box 130 which allows the user to view and change application configuration options.

As shown by FIG. 6, the configuration options are set in the Configuration Options dialog box 130 via, e.g. a Default Report Template drop down box 131 which the user may use to selects a default report template 112 from a group of such report templates, a Default Date Range drop down box 132 which the user may use to select a default date range 133, an Include Patient Name in Copied Information check box 134 to select whether such information is copied with the data, and a listing of the default Export File Directory location 135.

The Configuration Options dialog box 130 in one embodiment is accessible from the system tray of the operating system 52 and allows the user to select which Date Range 133 and Report Template 112 will be defaulted to in the select boxes of the File Display Dialog Box 111 (FIG. 5). The option to include the patient name in the report copied to the clipboard may be selected here as well. This feature of having the patient name included in the paste of information is provided as a safety check to help ensure that the right data was put in the right patient's Electronic Medical Record (EMR) 68. The export file directory 135 displays the export file directory of diabetes management software 58 58. Clicking the OK button 136 applies any setting changes and dismiss the dialog box 130, while the Cancel button 137 causes the original settings to be retained also dismissing the dialog box 130.

It is to be appreciated that the CConfiguration class 89 monitors for changes in the default export file directory location 135, and stores the configuration settings for the interface service 62. Further properties of the CConfigurationWindow class 90 include: CConfigurationWindow( ) which implements the Configuration Options dialog box 130; void RefreshDirectory( ) which sets the export directory on the dialog; void btnSave_Click which saves the currently selected configuration options and is selected via a user selectable OK button 136; and void btnCancel_Click which closes the dialog without saving configuration option changes and which is selected via a user selectable Cancel button 137.

The CDetectedFileQueue class 91 maintains a list of exported files that will need to be processed and has the following properties: CDetectedFileQueue( ) is a list of export files that have been exported while processing earlier files; void NewFile( ) in this class allows a file to be added to the processing queue; String NextFile( ) is the file name of the next file to be processed; bool HasMore( ) is a Boolean value that indicates if there are more files to be processed; and void FireFileDetected( ) is the event method used to notify the processor of new export file(s), such that the File Display dialog box 111 is opened.

The CAppErrorLog class 92 provides a static method for the interface service 62 to report errors to and writes reported errors to disk with a timestamp. The properties of this class include CAppErrorLog( ) class object which that the interface service 62 reports errors to; and void LogError( ) which is the method to call to log an error.

The CFileDisplayWindow class 93 implements the windows form for the File Display dialog box 111. In this class, CFileDisplayWindow( ) is the windows form implementing the File Display dialog box 111, void_fileQueue_FileDetected( ) provides notification for new export files, and void_config_FileSyncFailure( ) is an error handler for file synchronization failure. In addition, void_cmbTemplate_SelectedIndexChanged( ) is notification that the selected template has been changed, void cmbDateRange_SelectedIndexChanged ( ) provides notification that the selected number of days has been changed, and void btnDone_Click is used to dismiss the dialog and clean up temporary data via a user selectable Done button 138 provided on the File Display dialog box 111. A void btnCopy_Click is used to place (copy) formatted patient diabetes data 110, i.e. the patient diabetes data 66 formatted according to the selected date range 133 and report template 112 and displayed in the File Display dialog box 111, into the clipboard 64 (FIG. 2) via a user selectable Copy All button 113 also provided on the File Display dialog box 111.

The CFileFormatter class 94 is responsible for reading and parsing the patient diabetes data 66 in the export files into the structure of the PatientData class 95 that is defined by the selected report template 112 and date range 133, which results in the displayed formatted patient diabetes data 110. Examples of the selectable report templates from the Report Template drop down box 131 include: "Standard Day Statistics and Standard Day List", "Standard Day Statistics", "Trend Statistics and Standard Day Statistics", "Trend Statistics", "Standard Week Statistics", "Standard Day List", "Trend List", "Trend Statistics and Standard Week Statistics", "Trend Statistics and Standard Day List", "Trend Statistics and Trend List", "Trend Statistics, Standard Day Statistics, and Standard Day List". Examples of the selectable date range from the Date Range drop down box 132 include: 1 Week, 2 Weeks, 4 Weeks, 6 Weeks, 8 Weeks, or ALL. As shown by FIG. 6, if the date range in the parsed file is less than the currently selected Date Range, the interface service 62 will an indication 139 beside the Date Range drop down (i.e., choice) box 132 and/or a message 140 in the File Display dialog box 111.

For example, as shown by FIG. 5, in one embodiment the default report template is the Standard Day Statistics and Standard Day List template. In this illustrative report, the patient diabetes data 66 exported from the diabetes management software 58 via the export file 84 (FIG. 2) is reformatted according to the selected template, in which the selected date range 133 of the data used in the report template 112 is display in a text display field 142 of the File Display dialog box 111 showing the formatted patient diabetes data 110 as "date range from-to (MM/DD/YYY-MM/DD/YYYY)" where MM is the two digit month, DD is the two digit day, and YYYY is the four digit year. For the Standard Day List, the bG values for each reading is displayed also in the text display field 142, grouped in the time blocks defined in diabetes management software 58 (FIG. 2). For the Standard Day Statistics, the reading count (labeled "N"), mean bG (labeled "MBG"), standard deviation (labeled "SD"), and hi/lo count (labeled "Hi/Lo") for each time block are also displayed in the text display field 142.

The CFileFormatter class 94 also provides a derivable base class framework from which other data import classes can be generated. The properties and methods of this class include CFileFormatter( ) class object which implements the parsing of patient date into templates, PatientData which is a local reference to the PatientData class 95 that holds the parsed data, and PatientData.BlockOfTime CreateTimeBlock( ) which is used to create a time block to prepare for formatting.

The PatientData class 95 as mentioned holds exported and parsed patient report data, and can comprise various patient data property fields, such as, e.g., blood glucose measurements and measurement time information.

The ReportGenerator class 96 is derived from ReportGenerator which called by the CFileDisplayWindow class 93 with the patient information to be formatted. The ReportGenerator class 96 when called processes patient data to produce output reports, and provides a derivable base class framework from which other report generation classes can be created. The properties of this class include: ReportName which holds the name of the report, string GenerateReport( ) which is the method used to create the report as a string from the patient data, List FilteredResults( ) is the filter results from the data by input criteria, and List MostRecentNWeeks( ) is the filter results for the most recent specified number of weeks. This class also includes a string FormatStatistics( ) which provides a formatted string from a raw block of statistics, string StandardDayStatisticsReport( ) which provides the Standard Day Statistics report from the specified data, string StandardDayListReport( ) which produces the Standard Day List report from the specified data, string StandardWeekStatisticsReport( ) which produces the Standard Week Statistics report from the specified data, string TrendStatisticsReport( ) which produces the Trend Statistics report from the specified data, and string TrendListReport( ) which produce the Trend List report from the specified data.

In one embodiment, the interface service 62 is invoked by the operating system 52 during the computer startup and runs in the system tray (or background) as mentioned previously above. Accordingly, unless disabled per a user request or via a computer shutdown, the interface service 62 will always be running when any PC user is logged on. In another embodiment, the interface service 62 may also be started manually by the user. When started, the interface service 62 scans the default export directory location 135 and memorizes the existing data files in the directory. The interface service 62 then periodically (or continuously) monitors the directory location 135 (FIG. 6) for any new export files 84 (FIG. 2) saved thereto to detect a change in the directory. This detection will occur after a user transfers the patient diabetes data 66 containing, e.g., patient self monitoring blood glucose tests, from the patient data collection device 48 to the diabetes management software 58, and exports the patient data to a new export file 84.

For example, in one embodiment a data export dialog box may be presented to the user by the diabetes management software 58 when the user selects "Export" from a "File" menu provided by that program. Typically, the user then selects the data types to be exported and the date range, and clicks the OK button to continue. The diabetes management software 58 next may present a directory dialog box to allow the operator to select the file name and location for the exported file. Note that if the user selects a location other than the default, the export file 84 will not be seen by the interface service 62. A text dialog box will indicate to the user with the export process is completed.

When the new export file 84 appears in the monitored directory location 135, the interface service 62 will automatically parse and format the data contained in the export file and display it as formatted patient diabetes data 110 in the File Display dialog box 111 (FIG. 5) using the default template 112 and the default date range 133. It is to be appreciated that from the File Display dialog box 111, the user may select a new Date Range 133 and/or Report template 112 from the current default via the Date Range drop down (i.e., choice) box 132 and Report template drop down (i.e., choice) box 131, respectively. If the user changes the current either the date range or report template, the interface service 62 dynamically changed the displayed formatted patient diabetes data 110 to match the current selections.

As also shown by FIG. 5, the interface service 62 with also displays patient locator data 121 which includes the patient name 144, date of birth 146 and a Patient ID 148 for the current export file as assigned by the diabetes management software 58 58. The patient name 144 is also displayed in a title bar 150 of the file display dialog box 111 as well as brief instructions 152 for the use of the interface service 62. It is to be appreciated that the patient name 144, the patient date of birth 146, and the Patient ID 148 are provide as non-selectable, read only fields, whereas the parsed and formatted patient diabetes data 110 displayed in the text display filed 142 is read only, but selectable. Accordingly, alteration of the formatted patient data is not permitted within the interface service 62 for added data integrity.

When processing the data, through the report template drop down (i.e., choice) box 131 and date range choice box 132, the interface service 62 permits the user to indicate that the data from the export file 84 to be copied to the clipboard 64 (FIG. 2). The interface service 62 uses all data from the latest reading/result contained in the data of the export file 84 to the currently selected number of weeks indicated by the selected date range 133. If the current export file 84 contains a number of days that is less than the selected data range 133, as mentioned, the interface service 62 will provide the message 140.

A user selecting (e.g., a mouse click) the Copy All button 113 in the File Display dialog box 111 inserts the patient name (if check box 134 is selected in the Configuration Options dialog box 130) and the current date followed by all the formatted patient diabetes data 110 provided in the text display field 142 into the clipboard 64 replacing any existing content.

Figure 7:
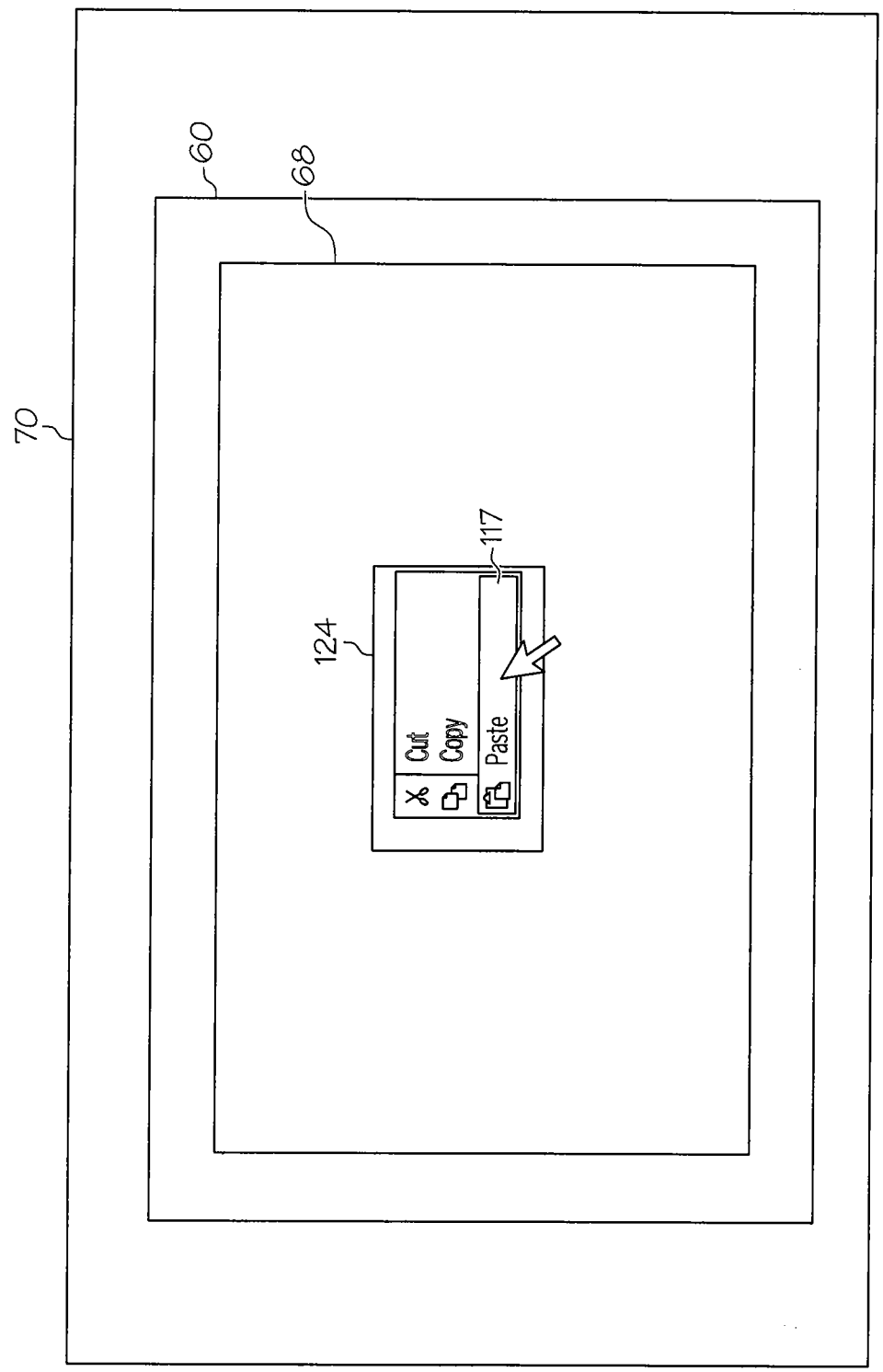
FIG. 7 is a screen shot depiction of a process according to the present invention to place patient diabetes information exported from a diabetes management system into an electronic medical record of a health record system.
Figure 8:
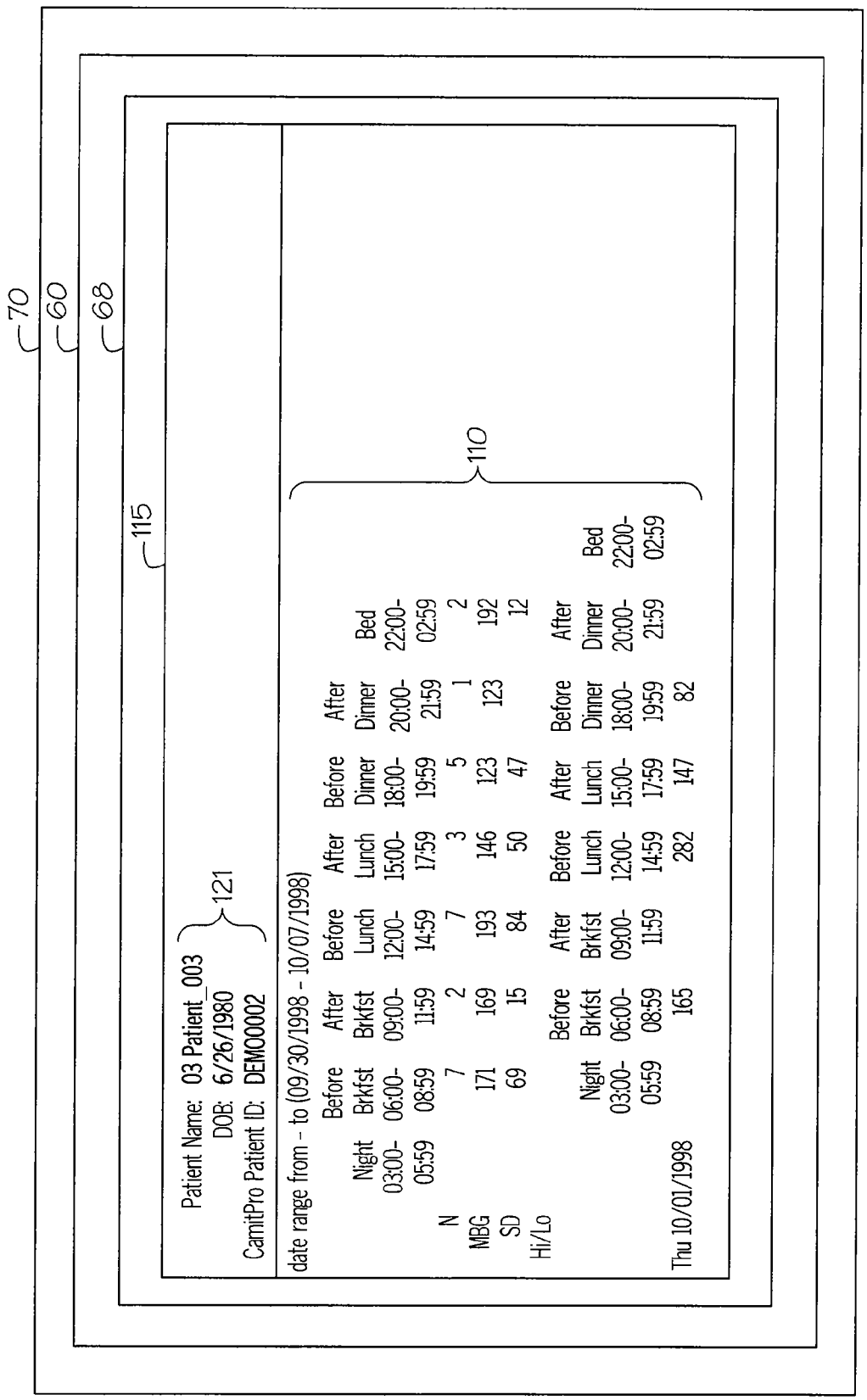
FIG. 8 is a screen shot depiction of patient diabetes information exported from a diabetes management system provided in an electronic medical record of a health record system according to the process of FIG. 7.

As shown by FIG. 7, the user then switches to (or opens) in the GUI environment 70 the client application 60 which has open the electronic medical record 68 for the current patient that is maintained in the database 24 (FIG. 1) of the health record system (i.e., server computer 12). The user then pastes the formatted patient diabetes data 110 into the electronic medical record of the patient via a paste command 117 provided by a dialog box 124 of the clipboard 64 (displayed e.g., via right clicking on a computer mouse). As shown by FIG. 8, the formatted patient diabetes data 110 as well as the patient locator data 121 is pasted by the user in the electronic medical record 68, such as to an appropriate section, such as a notes section 115.

After pasting, the user then switches back to the interface service 62 in the GUI environment. Referring back to FIG. 5, the interface service 62 permits the user to indicate that the export file 84 is to deleted when finished via a check box 154. By default, the interface service 62 deletes the export file 84. The interface service 62 also allows the user to indicate they are finished working with the current export file 84 via the Done button 138. In one embodiment, when the user indicates he/she is done with the current export file 84, the interface service 62 clears the clipboard 64 at the end of each file handling to reduce the chance that the user may be looking at one patient's data, but paste the previous patient's data into the current patient's electronic medical record 68. In addition, if the Delete export file on exit check box 154 is checked, the interface service 62 will also delete the export file 84 when the Done button 138 is selected.

In another embodiment, before exiting to clear the clipboard 64 and optionally deleting the export file 84, the interface service 62 requests confirmation when exiting via a confirmation dialog box (not shown). Clicking an OK button dismisses the confirmation and exit the interface service 62. Clicking a Cancel button shall dismiss the confirmation.

After exiting, the interface service 62 either reopens to process the next export file 84 located at the export file directory location 135 or if there are no other export files 84 to process, returns to the system tray and waits for the next export file to be provided to the export file directory 135. From the system tray, the interface service 62 also provides a selectable menu (e.g., right clicking on the interface service icon) providing an About box, a settings option which when selected opens the Configuration Options dialog box 130, and an exit option to close the interface service 62 and dismiss it from the system tray.

Figure 4:
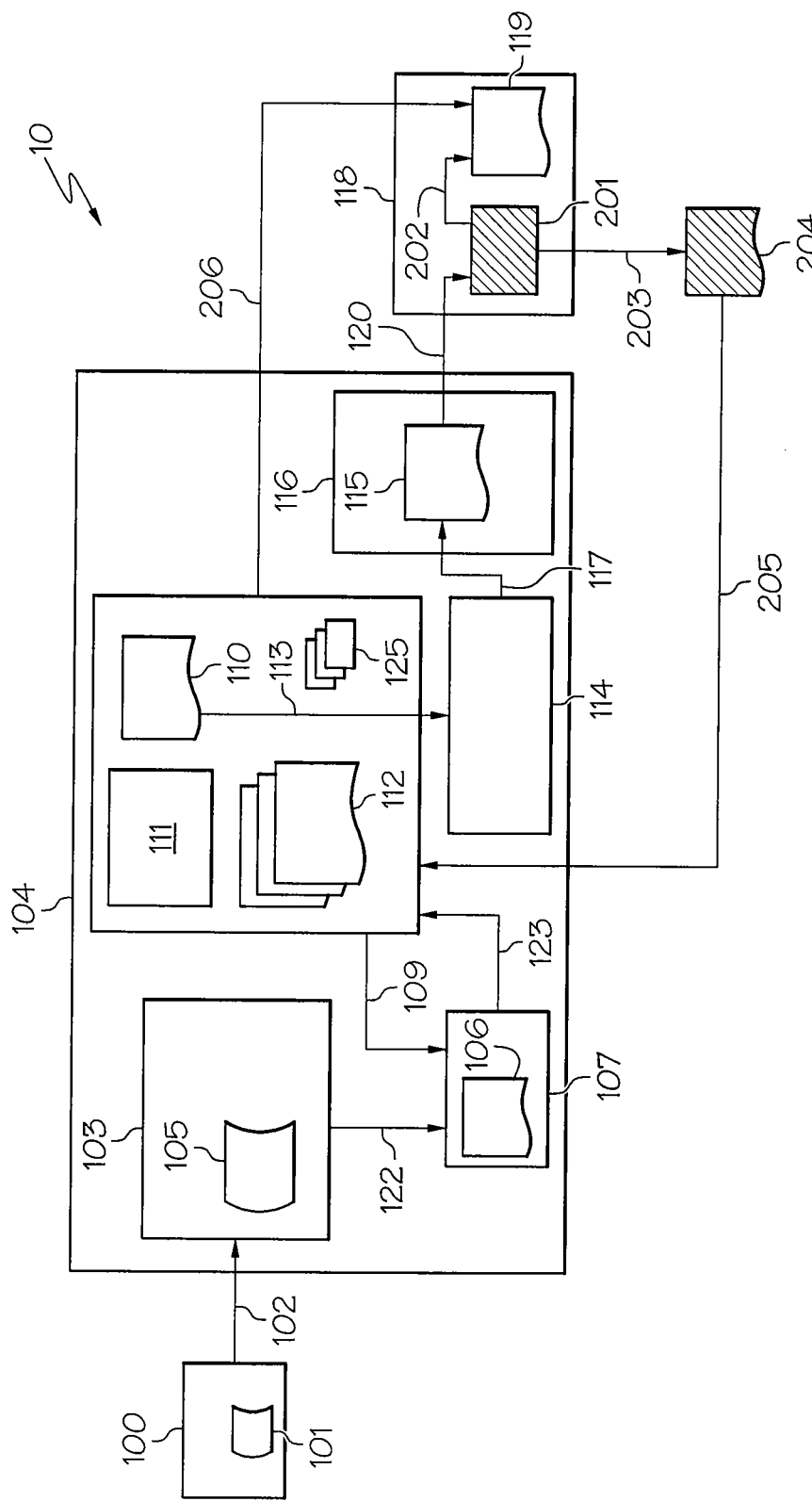
FIG. 4 is a block diagram of processes performed according to various embodiments of the present invention.

With reference now to FIG. 4, one embodiment of a method for formatting and transferring patient diabetes data 101 into an electronic medical record 115 provided by a health record system 118 with user validation is disclosed. In general, the method takes place after testing a patient's blood glucose levels over a period of time with a blood glucose meter 100, which stores the patient diabetes data 101 in a first electronic format, and after a user transfers 102 the patient diabetes data 101 from the blood glucose meter 100 into a patient record 105 contained in a diabetes management system 103, implemented via diabetes management software 58 on a computer 104. The method comprises then providing an interface service 108 (i.e., interface service 62 as enabled and described above) which automatically monitors 109 an output folder 107 to determine when an export file 106 is stored into an output folder 107 provided at a predetermined file directory location.

The user then selects the patient diabetes data 101 contained in the patient record 105 for creation of the export file 106 in a second electronic format and stores 122 the export file 106 in the output folder 107. After the interface service 108 automatically detects the export file 106 in the output folder 107, the interface service 108 automatically parses and formats 123 the patient diabetes data 101 contained in the export file 106 according to a preselected report template 112 and date range 125, and automatically opens a dialog box 111 which displays the patient diabetes data 101 as formatted patient diabetes data 110. The dialog box 111 allows the user to select from a plurality of report templates 112 and date ranges 125 by which to format the patient diabetes data 101 contained in the export file 106. The method further includes copying 113 the displayed formatted patient diabetes data 110 into a clipboard utility 114 provided by the computer 104, selecting and displaying the electronic medical record 115 of the patient in a client application 116 of the health record system 118 provided on the computer 104, and pasting 117 (which also displays) the formatted patient diabetes data 110 in the electronic medical record of the patient.

In another embodiment, the method further comprises the client application 116 of the health record system 118 storing 120 the pasted formatted patient diabetes data 110 in a database 119 of the health record system 118. In still another embodiment, the method further comprises including patient locator data 121 from the diabetes management system 103 in the formatted patient diabetes data 110. In another embodiment, the method further comprises providing an additional data processing service 201 that intercepts the original path of medical record storage 120 into a path 202 that continues to the medical record database 119 and an output path 203 that stores the path 202 and the patient locator data 121, which is also provided into a similar patient locator data field in the electronic medical records database 119, as mapping information 204. The method further comprises allowing the interface service 108 to access 205 the mapping information 204 and directing future records for the same patient using an alternate direct route 206 to store the formatted patient diabetes data 110 without a further need for user intervention.

The present invention may further be embodied as a computer readable medium, such as an installation file downloadable from a web site, or a store device such a compact disc, floppy disk, magnetic tape, portable memories, and the likes, which provide instructions which will configured a computer system (e.g., client computer 14) to implement the above described methods.

It is to be appreciated that for the embodiments described above, the functionalities itself as well as the graphical user interface environment may be modified in many ways. Particularly, they may be adapted to the computing and display equipment used, especially to its input means, kind of display, display size, computing power, memory size etc. As such, the above description and drawings are only to be considered illustrative of exemplary embodiments, which achieve the features and advantages of the present invention. Modification and substitutions to specific process steps, system, and setup can be made without departing from the spirit and scope of the present invention. Accordingly, the invention is not to be considered as being limited by the foregoing description and drawings, but is only limited by the scope of the appended claims.

What is claimed is:

1. A method for formatting and transferring patient diabetes data into an electronic medical record on a health record system with user validation, after testing a patient's blood glucose levels over a period of time with a blood glucose meter which stores the patient diabetes data containing blood glucose levels in a first electronic format and after a user transfers the patient diabetes data from the blood glucose meter into a patient record provided by a diabetes management system on a computer, creates an export file which provides the patient diabetes data in a second electronic format and stores the export filed to an output folder, said method comprising:
   providing an interface service which automatically monitors the output folder to determine when the export file is provided thereto;
   automatically detecting with the service the export file when provided to the output folder;
   after detection, automatically parsing, formatting, and receiving with the interface service the export file into formatted patient diabetes data according to a pre-defined-report template;
   automatically opening a dialog box on an electronic display which displays the formatted patient diabetes data;
   copying the displayed formatted patient diabetes data into a clipboard utility provided by the computer;
   selecting, displaying, and transferring the electronic medical record of the patient in a client application of the health record system provided on the computer to a processor; and
   pasting, displaying, and processing the formatted patient diabetes data in the electronic medical record of the patient to produce a complete electronic medical record.

2. The method of claim 1 further comprising permitting automatic reformatting of the formatted patient diabetes data by selection of another report template from a plurality of report templates listed in a choice box provided by the dialog box.

3. The method of claim 2 further comprises selecting another report template.

4. The method of claim 1 wherein the automatically parsing and formatting with the interface service of the export file is also according to a pre-defined date range.

5. The method of claim 1 wherein the automatically parsing and formatting with the interface service of the export file is also according to a pre-defined date range, and said method further comprises permitting automatic reformatting of the formatted patient diabetes data by selection of another date range from a plurality of date ranges listed in a choice box provided by the dialog box.

6. The method of claim 1 wherein the user interface of the health record system stores the pasted formatted patient diabetes data in a database of the health record system.

7. The method of claim 1 further comprises accessing the health record system over a network from another computer.

8. The method of claim 1 further comprising providing the health record system on the computer.

9. The method of claim 1 further comprising closing the dialog box along with automatically clearing the clipboard service and removing the export file from the export folder.

10. The method of claim 1 further comprising including patient locator data from the diabetes management system in the formatted patient diabetes data.

11. The method of claim 1 further comprising providing an additional data processing service that intercepts a storage path of the electronic medical record which continues into the medical record database and provides an output path that stores the storage path and patient locator data as mapping information.

12. The method of claim 11, further comprising allowing the interface service to access the mapping information and directing future records for the same patient using an alternate direct route to store the formatted patient diabetes data without a further need for user intervention.

13. A non-transitory computer readable medium providing instructions for formatting and transferring patient diabetes data into an electronic medical record of a health record system, said instructions when executed on a processor, causes the processor to:
   provide an output folder which receives from a diabetes management system the patient diabetes data which contains a plurality of blood glucose levels resulting from tests taken over a period of time by the patient with a blood glucose meter, wherein the patient diabetes data containing the blood glucose levels is stored as an export file in the output folder by the diabetes management system in an electronic format different from the electronic format in which the patient diabetes data was transferred from the blood glucose meter into a patient record provided by the diabetes management system;
   provide an interface service which automatically monitors the output folder to determine when the export file is provided thereto;
   automatically detect with the service the export file when provided to the output folder;
   after detection, automatically parse, format, and receive with the interface service the export file into formatted patient diabetes data according to a pre-defined report template;
   automatically open a dialog box on an electronic display which displays the formatted patient diabetes data;
   copy the displayed formatted patient diabetes data into a clipboard utility provided by the computer;
   select, display, and transfer the electronic medical record of the patient in a client application of the health record system; and
   paste, display, and process the formatted patient diabetes data in the electronic medical record of the patient to produce a complete electronic medical record.

14. A method for formatting and transferring patient diabetes data of a patient into an electronic medical record on a health record system, said method comprising:
   providing an output folder on a computer which receives from a diabetes management system the patient diabetes data which contains a plurality of blood glucose levels resulting from tests taken over a period of time by the patient with a blood glucose meter, wherein the patient diabetes data containing the blood glucose levels is stored as an export file in the output folder by the diabetes management system in an electronic format different from the electronic format in which the patient diabetes data was transferred from the blood glucose meter into a patient record provided by the diabetes management system;
   displaying a configuration option dialog box on an electronic display which displays a group of report templates;
   receiving on the computer from the configuration options dialog box a default report template selected by the user from the group of report templates, a default data range, and a selection to indicate whether to include name of the patient in the electronic medical record;

providing an interface service which is invoked automatically at start up of the computer and which automatically monitors the output folder to determine when the export file is provided thereto;

automatically detecting with the service the export file when provided to the output folder;

after detection, automatically parsing, formatting, and receiving with the interface service the export file into formatted patient diabetes data according to the default report template and the pre-defined date range along with the name of the patient if the selection indicates that the name of the patient is to be included in the electronic medical record;

automatically opening a dialog box on the electronic display which displays the formatted patient diabetes data;

copying the displayed formatted patient diabetes data into a clipboard utility provided by the computer;

selecting, displaying, and transferring the electronic medical record of the patient in a client application of the health record system provided on the computer to a processor; and pasting, displaying, and processing the formatted patient diabetes data in the electronic medical record of the patient to produce the electronic medical record.

\* \* \* \* \*

UNITED STATES PATENT AND TRADEMARK OFFICE
CERTIFICATE OF CORRECTION

PATENT NO.        : 8,583,455 B2                                   Page 1 of 3
APPLICATION NO.   : 12/233882
DATED             : November 12, 2013
INVENTOR(S)       : Alan M. Greenburg et al.

It is certified that error appears in the above-identified patent and that said Letters Patent is hereby corrected as shown below:

On the Title Page

(75) Inventors: "Alan M. Greenburg, Indianapolis, IN (US);
   Brittany A. Dressler, Indianapolis, IN (US);
   Igor Gejdos, Indianapolis, IN (US);
   Anthony J. Butt, Noblesville, IN (US);
   Kristin Davenport, Fortville, IN (US)" should read

(75) Inventors: --Alan M. Greenburg, Indianapolis, IN (US);
   Brittany A. Dressler, Indianapolis, IN (US);
   Igor Gejdos, Indianapolis, IN (US);
   Anthony J. Butt, Noblesville, IN (US);
   Kristin Westerfield, Fortville, IN (US)--;

In the Specification

Col. 1, Line 45,
"tially by persons not typically familiar such programs. Fur-" should read
--tially by persons not typically familiar with such programs. Fur- --;

Col. 2, Line 1,
"diabetes management system on a compute, creates an export" should read
--diabetes management system on a computer, creates an export--;

Col. 2, Line 3,
"electronic format and stores the export filed to an output" should read
--electronic format and stores the export file to an output--;

Signed and Sealed this
Twentieth Day of January, 2015

Michelle K. Lee
*Deputy Director of the United States Patent and Trademark Office*

Col. 2, Line 23,
"tions which will configured a computer system to implement" should read
--tions which will configure a computer system to implement--;

Col. 5, Line 36,
"system (e.g. sever computer 12) via the Internet 30 to provide" should read
--system (e.g. server computer 12) via the Internet 30 to provide--;

Col. 6, Line 30,
"up to the time of one fully time employee to manually enter" should read
--up to the time of one full time employee to manually enter--;

Col. 7, Line 18,
"service 62 runs as a windows system tray applications and" should read
--service 62 runs as a windows system tray application and--;

Col. 7, Line 33,
"95, and ReportGenrator class 96" should read
--95, and ReportGenerator class 96--;

Col. 7, Line 59,
"to selects a default report template 112 from a group of such" should read
--to select a default report template 112 from a group of such--;

Col. 8, Line 10,
"136 applies any setting changes and dismiss the dialog box" should read
--136 applies any setting changes and dismisses the dialog box--;

Col. 9, Line 13,
"will an indication 139 beside the Date Range drop down (i.e.," should read
--will have an indication 139 beside the Date Range drop down (i.e.--;

Col. 9, Line 22,
"range 133 of the data used in the report template 112 is display" should read
--range 133 of the data used in the report template 112 is displayed--;

Col. 10, Line 31,
"service 62. A text dialog box will indicate to the user with the" should read
--service 62. A text dialog box will indicate to the user when the--;

Col. 10, Line 47,
"As also shown by FIG. 5, the interface service 62 with also" should read
--As also shown by FIG. 5, the interface service 62 also--;

CERTIFICATE OF CORRECTION (continued)
U.S. Pat. No. 8,583,455 B2

Col. 10, Line 55,
"birth 146, and the Patient ID 148 are provide as non-select-" should read
--birth 146, and the Patient ID 148 are provided as non-select- --;

Col. 11, Line 27,
"export file 84 is to deleted when finished via a check box 154." should read
--export file 84 is to be deleted when finished via a check box 154.--;

Col. 11, Line 44,
"dismisses the confirmation and exit the interface service 62." should read
--dismisses the confirmation and exits the interface service 62.--;

Col. 12, Line 51,
"able from a web site, or a store device such a compact disc," should read
--able from a web site, or a store device such as a compact disc,--; and Col. 12, Line 53,
"which provide instructions which will configured a computer" should read
--which provide instructions which will configure a computer--.